US006423833B1

(12) United States Patent
Catani et al.

(10) Patent No.: US 6,423,833 B1
(45) Date of Patent: Jul. 23, 2002

(54) FUNCTIONAL SUGAR POLYMERS FROM INEXPENSIVE SUGAR SOURCES AND APPARATUS FOR PREPARING SAME

(76) Inventors: Steven J. Catani, 265 Red Oak Trail, Athens, GA (US) 30606; Kathleen S. Laurenzo, 149 Buttonwood Loop, Athens, GA (US) 30605; Juan L. Navia, 169 Lenox Pl., Athens, GA (US) 30606; Robert E. Walkup, 22761 Summer La., Novi, MI (US) 48374-3648

( * ) Notice: Subject to any disclaimer, the term of this patent is extended or adjusted under 35 U.S.C. 154(b) by 0 days.

(21) Appl. No.: 09/305,788

(22) Filed: May 4, 1999

Related U.S. Application Data
(60) Provisional application No. 60/084,281, filed on May 5, 1998.

(51) Int. Cl.[7] .......................... C07H 17/00; C07H 1/00; C12P 19/18
(52) U.S. Cl. .................. 536/18.5; 536/123; 536/123.1; 536/124; 435/97; 435/101
(58) Field of Search .................. 536/18.5, 123, 536/123.1, 124; 435/97, 101

(56) References Cited

U.S. PATENT DOCUMENTS

| | | | |
|---|---|---|---|
| 4,309,505 A | 1/1982 | Smith et al. ................. 435/193 |
| 4,317,880 A | 3/1982 | Heady ......................... 435/94 |
| 4,335,207 A | 6/1982 | Heady ......................... 435/94 |
| 4,356,262 A | 10/1982 | Heady ......................... 435/97 |
| 4,423,150 A | 12/1983 | Heady ......................... 435/193 |
| 4,617,269 A | * 10/1986 | Rathbone et al. ............. 435/97 |
| 4,681,771 A | 7/1987 | Adachi et al. ............... 426/658 |
| 4,849,356 A | 7/1989 | Van Dooren et al. ........ 435/183 |
| 5,180,674 A | 1/1993 | Roth .......................... 435/288 |
| 5,288,637 A | 2/1994 | Roth .......................... 435/288 |
| 5,514,660 A | 5/1996 | Zopf et al. ................... 514/25 |
| 5,968,365 A | 10/1999 | Laurenzo et al. ........... 210/641 |

FOREIGN PATENT DOCUMENTS

| | | | |
|---|---|---|---|
| EP | 188 047 | * 7/1986 | |
| EP | 0 272 095 A2 A3 | 6/1988 | ........... C12P/19/18 |
| EP | 0 440 074 B1 | 8/1991 | ........... C12P/19/00 |
| EP | 0 452 238 A2 A3 | 10/1991 | ........... C13K/1/00 |
| EP | 0 787 745 A2 A3 | 8/1997 | ........... C08B/37/18 |
| GB | 2 179 946 A | 3/1987 | ........... C12P/19/18 |
| JP | 60-027395 | * 1/1985 | |
| JP | 60-414497 | * 3/1985 | |
| JP | 02-150289 | * 8/1990 | |
| JP | 04-237496 | * 8/1992 | |

OTHER PUBLICATIONS

Rademann et al. "A New Method for the Solid Phase Synthesis of Oligosaccharides", Tetr. Lett., vol. 37(23): 3989–3990, 1996.*

Ding et al. "Synthesis and Biological Activity of Oligosaccharide Libraries", Glycoimmunology, Phenum Press, pp. 261–269, 1995.*

Nicolaou et al. "Solid–Phase Synthesis of Oligosaccharides: Construction of a Dodecasaccharide", Angew. Chem. Int. Ed., vol. 37(11): 1559–1560, 1998.*

Murata et al. "Preparation of Oligosaccharide Units Library and Its Utilization", Biosci. Biotech. Biochem., vol. 61(7): 1059–1066, 1997.*

(List continued on next page.)

*Primary Examiner*—Ralph Gitomer
*Assistant Examiner*—Devesh Khare

(57) ABSTRACT

A process for preparing functional sugar polymers comprising transferring a monosaccharide or oligosaccharide to an acceptor, removing by-products, separating polymers which have not achieved the desired chain length and recycling these underdeveloped polymers, and an apparatus for producing same.

17 Claims, 6 Drawing Sheets

OTHER PUBLICATIONS

Sofia, Michael. "Chemical Strategies for Introducing Carbohydrate Molecular Diversity into the Drug Delivery Process", Retrieved from the Internet URL: http://www.netsci.org/Science/Combichem/feature12.htm [retrieved on Jul. 13, 1998].*

Kahne, Daniel. "Combinatorial Approaches to Carbohydrates", Curr. Opin. Chem. Bio., vol. 1: 130–135, 1997.*

Rodebaugh et al. "Polymer–Supported Oligosaccharides via n–pentenyl Glycosides: Methodology for a Carbohydrate Library", J. Org. Chem., vol. 62: 5660–5661, 1997.*

Seeberger et al. "Synthesis of Biologically Important Oligosaccharides and Other Glycoconjugates by the Glycal Assembly Method", Aldrichimica Acta, vol. 30(3): 75–92, 1997.*

Fitz et al. "Oligosaccharide Synthesis by Enzymatic Glycosidation", (Chapter 21 of Preparative Carbohydrate Chemistry, ed. by Stephen Hanessian), Marcel Dekker, pp. 485–504, 1997.*

Palcic, Monica. "Glycosyltransferases in Glycobiology", vol. 230 of Methods in Enzymology (Guide to Techniques in Glycobiology), Acad. Press, pp. 300–316, 1994.*

Palcic, Monica. "Glycosyltransferases in the Synthesis of Oligosaccharide Analogs", Calbiochem Catalog (section 1), 1999.*

Patent Abstracts of Japan;02150289; Jun. 8, 1990; Applicant—Meiji Seika Kaisha Ltd.; Inventor—Otsuka Ryuichi; "Production of High–Purity Fructo–Oligosacchasride".

Patent Abstracts of Japan; 03180189; Aug. 31, 1990; Applicant—Toto Ltd.; Inventor—Nogaki Hisashi; Production of High–Purity Fructoligosaccharide.

Tetrahedron vol. 45, No. 17, pp 5365 to 5422, 1989–Tetrahedron Report No. 259– Enzyme–Catalyzed Synthesis of Carbohydrates–Eric J. Toone,Ethan S. Simon, Mark D. Bednarski, George M. Whitesides, Dept of Chem, Harvard Univ.

Science and Technology of Fructans– pp 273–302– 0–8493–5111–1/9, 1993 by CRC Press, Inc.—Chapter 9, "Production and Utilization of Microbial Fructans", Masao Hirayama and Hidemas Hidaka.

Enzyme and Microbial Technology 19:107–117, 1996–Elsevier Science Inc. pp 107–117—"Fructooligasaccharides–Occurrence, preparation, and application"—Jong Won Yun.

Enzyme Microb. Technol., 1994, vol. 16, Apr., pp 334–339 "Kinetic studies and mathematical model for enzymatic production of fuctooligasaccharides from sucrose"Kow Jen Duan, Jen Shin Chen and Dey Chyi Sheu.

Chemistry & Industry, Mar. 3, 1997, pp 170–175, Carbohydrate drugs—an ongoing challenge—Joseph C.McAuliffe & Ole Hindsgaul.

Symposium of Association A. v.H., Reims, 1995, Zuckering. 120 (1995) Nr. 9, pp 793–798—Fructo–oligosaccharides: Enzymic synthesis from sucrose– Francoise Ouarne and Alain Guibert.

* cited by examiner

FUNCTIONAL SUGAR POLYMERS FROM INEXPENSIVE SUGAR SOURCES AND APPARATUS FOR PREPARING SAME

This application claims benefit of provisional application 60/084,281 filed May 5, 1998 and is a continuation-in-part of U.S. Pat. No. 5,968,365, filed Jan. 15, 1997.

FIELD OF THE INVENTION

This invention relates to a process for preparing functional sugar polymers and an apparatus useful for the synthesis of such sugar polymers.

BACKGROUND OF THE INVENTION

Sugar polymers produced by microorganisms and plants, mainly straight and branched glucans and fructans, have a long history of applicability in food products as gums, fillers, bulk sources, and other similar usage. In addition to their uses in foods some of these sugars have long been purported to impart health benefits. See, McAuliffe, J., Hindsgaul, O.; "Carbohydrate Drugs—An Ongoing Challenge", *Chemistry and Industry*, Mar. 3, 1997. More recently a growing number of these polymers (whether of plant, microorganism or mammalian origin), especially those having unique branching or containing other sugars, such as fucose, galactose, sugar amines, or sialic acid, have been cited as imparting a variety of health benefits (see, for example, U.S. Pat. No. 5,514,660). While a great deal is known concerning the specific use and functionality of many of the significant natural sugar polymers, the complexity of these compounds and the resultant difficulty and high cost of preparing structures which may not exist in nature has limited the knowledge of general structure/function or health benefit relationships. Sugar polymers are generally isolated from plants or microorganisms by extraction and purified by a variety of techniques. Significant work has been done to increase the availability and functionality and to decrease the cost of these polymers. This work has centered in the following areas:

- Better sources of the plant sugars have been found through the discovery of new species, selective breeding, and genetic manipulation.
- Improved processes to extract the sugar polymers have been developed.
- The sugar polymers have been separated into discrete chain length fractions and/or "refined" to a tighter specification.
- Simple chemical modifications to some plant sugars have been developed.

Work is ongoing and accelerating in all of these areas. One important area with significant on-going effort is the genetic modification of organisms to improve the production of the existing sugars or to make new sugars.

Methods to obtain sugar polymers without using plants are also known. Both chemical and enzymatic synthesis have been developed (see, for example, Whitesdie, G. M., et al.; "Enzyme-Catalyzed Synthesis of Carbohydrates", *Tetrahedron*, 45(17), pp. 5365–5422, 1989). Chemical synthesis, while possible is hindered by three factors. First, each of the monomeric units has multiple reaction sites. In normal chemical synthesis multiple reactive sites always add complexity but with carbohydrates this complexity is extremely significant. A polymer with just four sugar "monomer" units, can be assembled in ~270,000 possible ways. This complexity can be overcome by selective blocking and de-blocking of reactive sites but only at the expense of low yield and high processing cost. Second, the inter-sugar bonds are very labile under typical processing conditions again limiting synthetic choices and, decreasing yields. Finally, many chemical reactions are not stereo-specific, creating a separation problem and further yield reductions. The net results are high cost and general lack of availability. Chemical synthesis is clearly appropriate for production of sugar polymers only when the product carries a very high value.

Processes that use enzymes as selective catalysts offer more promise for the synthetic production of sugar polymers. Recent advances in the identification and production of these enzymes, as well as systems in which to accomplish multi-step coupling reactions have reduced the cost of producing sugar polymers by many orders of magnitude. These techniques are applicable to both "natural" polymers and novel polymers based on coupling "natural" carbohydrate sub-units in new ways. Enzymes have been identified which allow coupling of inexpensive starting materials, such as sucrose, making this type of process potentially very inexpensive. Enzyme based production provides for both coupling and stereo selectivity which minimizes purification costs (see U.S. Pat. No. 5,288,637, Roth, S., "Apparatus for the Synthesis of Saccharide Compositions"; U.S. Pat. No. 5,180,674, Roth, S., "Saccharide Compositions, Methods, and Apparatus for Their Synthesis"; PCT/US92/10891, Roth, S., "A Method for Obtaining Glycosyltransferases"; PCT/US95/12317, Gotschlich, E. C., "Glycosyltransferases for Biosynthesis of Oligosaccharides and Genes for Encoding Them"; PCT/US94/07807, Roth, S., "A Method for Synthesizing Saccharide Compositions"). While these techniques allow great control of the coupling reactions, control of the chain length or branch distribution in polymers is not addressed.

An example of a sugar polymer is inulin. This polymer consists of fructose units, joined linearly in a $\beta\text{-}[2\text{-}\!\!\rightarrow\!1]$ fashion to a terminal $\alpha$-D-glucopyranosyl unit. In many plants inulin is a major energy storage carbohydrate. It is highly regarded as a naturally low calorie foodstuff, which can be used to provide bulk to high intensity sweeteners, as a soluble fiber source, as a fat replacer, and as a promoter of bifidus bacteria in the digestive tract. Inulin is commonly produced by extraction from plants, notably chicory and Jerusalem artichoke. The material extracted from these plants contains polymers with from 1 to over 60 fructose units attached to a terminal glucose unit. Polymer distributions vary with the plant source, the planting location, and the harvest time. While the crude extract has application, product with 3 to 10 fructose units provides the most "sucrose-like" performance. These polymers make ideal bulking agents and fiber sources as they have low caloric density, are bland, and have many of the functional attributes of sucrose. Shorter polymers, while functional, provide a disproportionate increase in calories and sweetness. Longer polymers are less water-soluble and have good fat replacer properties but decreased. sucrose replacement functionality.

Several approaches have been used to provide improved functionality and consistent inulin product over a growing season. The first approach involves using a plant source that contains relatively long chain inulin and using selective enzymes to reduce the chain size in a controlled manner. EP 440074 relates to the selective hydrolysis of long-chain inulins. This allows some control over seasonal variations at the cost of adding a process step and does not help to eliminate the high calorie, short chain products. Another approach is to fractionate the crude inulin into cuts with different functionality. While this solves the functionality and seasonal variation problems, it does so at the expense of creating by-products. This approach also provides for removal of short chain polymers. Since it only involves fractionation it adds no "foreign" substances to the product. The two approaches can be combined in several ways to optimize functional product recovery. In both of these cases the agricultural source is grown specifically for the inulin product with all the risks associated with any agricultural program. These approaches also present the problem of disposal of a large mass of unused vegetable material. Finally, except for very high use sugars such as sucrose, it is difficult to generate any economies of scale when growing a plant for a specific product.

Another method to produce inulin fructooligosaccharides is to build up the fructose polymer from an inexpensive fructose source, such as sucrose, using coupling enzymes. (See Jong Won Yun, "Fructooligosaccharides—Occurrence, Preparation, and Application", *Enzyme and Microbial Technology* 19:107–117, 1996, and U.S. Pat. No. 4,681,771). This approach suffers from inhibition of the enzymatic reaction by a by-product of the coupling, glucose, which limits the conversion of the sucrose feed, and the length of the chains produced. These inulin fructooligosaccharide compositions, commonly have an average chain length of under 5 fructose units.

Enzyme catalyzed reactions in biological systems are regulated by the inhibitory effects on the enzyme by the accumulation of by-products. This is used to the organism's advantage to prevent the accumulation of unused reaction products. Where the enzyme is used as part of a cascade of reactions, the product of an enzyme is removed by the actions of the next enzyme in the cascade. When enzymes are used in man-made reactors, alternative methods must be employed. One approach used to remove the inhibition is to scavenge the glucose that inhibits the forward reaction by converting it to another by-product. While this may improve yield, it does little to improve selectivity of chain length. Other techniques that remove glucose, such as permeation though a selective membrane, are also possible, but again only results in improved yield and fail to produce the desired polymers. Another refinement, commonly used in multi-step enzymatic reactors, is to use a series of reactors with inter-reactor removal of by-products, and if desirable, addition of feed materials. For a significant increase in system complexity this type of system can result in improved yield. While it also allows some control over the average of the polymer size, it offers little control of the chain length distribution.

Chain length distribution cannot be predicted using simple Michaelis-Menten kinetics (F. Ouarne and A. Guibert, "Fructooligosaccharides Enzymic Synthesis from Sucrose." *Zuckerindustrie* (Berlin) (1995), 120, pp 793–798).

Chain elongation of the fructooligosaccharide chains by sequential transfer of fructose from sucrose by *A. niger* fructosyltransferase is reported by M. Hirayama and H. Hidaka, (Chapter 9, "Production and Utilization of Microbial Fructans" in Science and Technology of Fructans, CRC Press, 1993):

2 GF→G+GF$_2$
GF+GF$_2$→G+GF$_3$
GF+GF$_3$→G+GF$_4$, etc.

As used above, the term GF refers to sucrose and the term GF$_n$ refers to a β-2,1-linked fructose oligosaccharide which is linked via its reducing end to an alpha-D-glucopyranosyl moiety.

A different model for the elaboration of fructooligosaccharide chains is proposed in K. J. Duan, J. S. Chen and D. C. Cheu., "Kinetic Studies and a Mathematical Model for Enzymatic Production of Fructooligosaccharides from Sucrose; Fructooligosaccharide Sweetener Production Using Aspergillus japonicus beta-D-fructofuranosidase." Enzyme Microb. Technol., 4, 334–339 (1994)). Two like-sized chains react with the enzyme to give a shorter and a longer chain, and a hydrolysis step that liberated fructose from the tetrasaccharide GF3:

2 GF$_n$→GF$_{n-1}$+GF$_{n+1}$ for n=1 to 3
GF$_3$→F+GF$_2$

F. Ouarne and A. Guibert ("Fructooligosaccharides: Enzymic Synthesis from Sucrose." Zuckerindustrie, (Berlin), 120, 793–798, (1995)) discloses a mathematical model based on the reaction pattern above, and added the transfer of fructose from the trisaccharide GF2 to glucose to produce two moles of sucrose and the hydrolysis reaction of sucrose to its component monosaccharides:

G+GF$_2$→2 GF
GF→F+G

The model described in Zuckerindustrie showed good agreement with observed experimental values in the production of the various components in the reaction mixture, but do not preclude the stepwise elongation of chains by sequential transfer of fructose from sucrose as a possible contributing mechanism.

The model described in Zuckerindustrie is based on well documented enzyme kinetics and predicts the performance reported for the production of fructooligosaccharides. A quick analysis of the model will reveal why these chain length distributions are obtained. The rate of formation of GF$_{n+1}$ is dependent on the concentration of GF$_n$. In both batch and plug flow reaction systems, this relation sets the type of distributions which will be seen. Pushing the reaction harder through increased concentrations, catalyst levels, or residence time doesn't affect the relative distribution, only its position. In the case of fructose polymers, this means that by increasing the extent of the reaction you can shift the product distribution from mostly GF$_2$ with progressively smaller amounts of GF$_3$, GF$_4$, etc., to mostly GF$_3$ with progressively smaller amounts of longer chains by pushing the reaction harder. Plug flow type reactor configurations, or multiple back-mixed reactors used in series increase the amounts of high polymers but again cannot impact the basic relation. If the polymerization reaction is considered essentially irreversible, the average length is clearly limited by these relations. When the GF supply is exhausted, no further growth will take place. If more sucrose is added, the reaction will go forward through GF$_2$. Assuming the problem of glucose inhibition can be overcome, this can be improved on by adding sucrose between the stages of a series of plug flow or back-mixed reactors. While this is feasible, it would certainly add significant cost and complexity to the system to achieve any meaningful improvements. Where reversible polymerization is possible, it may be possible to push the reaction further, but a new set of limitations would exist. In this case, an equilibrium level of products would be achieved, assuming sufficient residence time was given. Adding more sucrose would increase the total material produced but not the ratios of product. Likewise, other reactor configurations would also not change the final reaction mix.

SUMMARY OF THE INVENTION

The invention relates to a process for preparing a straight or branched sugar polymer of a desired chain length, preferably four or more units, comprising:

a) transferring a monosaccharide or oligosaccharide residue from a carbohydrate donor to an acceptor by means of selective catalytic transfer, preferably by reacting with an enzyme;

b) optionally, removing by-products from step a) which may inhibit yield or selectivity;

c) separating polymers which have not achieved the desired chain length; and d) recycling the polymers which have not achieved the desired chain length.

In another aspect, the invention relates to an apparatus for producing straight or branched sugar polymers of a desired chain length comprising:

a) a reactor in which a monosaccharide or oligosaccharide residue is transferred by selective catalytic transfer from a carbohydrate donor to an acceptor;

b) means for removing by-products from the reaction of step a);

c) means for separating polymers which have not achieved the desired chain length; and d) means for recycling the polymer chains which have not achieved the desired chain length back to the reactor.

We have discovered that by combining a means for separating underdeveloped polymers and by-products, for example, by selective membrane, such as nano-filters, with an enzyme based reactor you not only increase yield but also tailor the resultant product to a highly specific range. Using membranes in conjunction with the enzyme system provides two key benefits. First a membrane is used to remove the by-product, glucose, without converting it to another entity. This allows the reaction to proceed to high yields without adding reaction steps to the process. A second membrane is added to remove chains of the desired length from the system while recycling shorter (underdeveloped) chains back for further growth.

This novel combination results in a system that out performs the conventional approaches by a significant margin. Again, looking to the kinetic model, the reasons that this novel combination gives superior performance is clear. When a separation system is added as described herein the entire dynamic is changed. For example, $GF_3$'s produced are not removed from the system but are the source to produce $GF_4$'s which are taken as product. The concentrations in the reactor necessary to produce longer chains can be present without impacting the product distribution. The fundamental relations in the reactor remain, but do not effect the product mix. This is true regardless of whether the reaction is considered reversible or irreversible. Through judicious choice of membrane, any average polymer chain length distribution can be achieved while maintaining virtually 100% yield.

DETAILED DESCRIPTION OF THE INVENTION

As used herein, the term "acceptor" shall mean a carbohydrate which accepts a monosaccharide or oligosaccharide from a carbohydrate donor, said acceptor may be a monosaccharide, disaccharide, oligosaccharide or polysaccharide.

In accordance with preferred embodiments, the "carbohydrate donor" may be, for example, a sugar nucleotide, a glycosyl phosphate, a disaccharide or an oligosaccharide.

Examples of suitable monosaccharides include glucose, galactose, fructose, fucose, sialic acid, N-acetyl glucosamine, N-acetyl galactosamine, glucuronic acid, iduronic acid, xylose and mannose.

The invention relates to a process for preparing a straight or branched sugar polymer of a desired chain length, preferably four or more units, comprising:

a) transferring by selective catalytic transfer, preferably by reacting with an enzyme, a monosaccharide or oligosaccharide residue from a carbohydrate donor to an acceptor;

b) removing by-products which may inhibit yield or selectivity, from the reaction of step a);

c) separating polymers which have not achieved the desired chain length; and d) recycling the polymers which have not achieved the desired chain length.

In another aspect, the invention relates to an apparatus for producing straight or branched sugar polymers of a desired chain length comprising:

a) a reactor in which a monosaccharide or oligosaccharide residue is transferred by selective catalytic transfer from a carbohydrate donor to an acceptor;

b) means for removing by-products from the reaction of step a);

c) means for separating polymers which have not achieved the desired chain length; and d) means for recycling the polymer chains which have not achieved the desired chain length back to the reactor.

Figure 1:
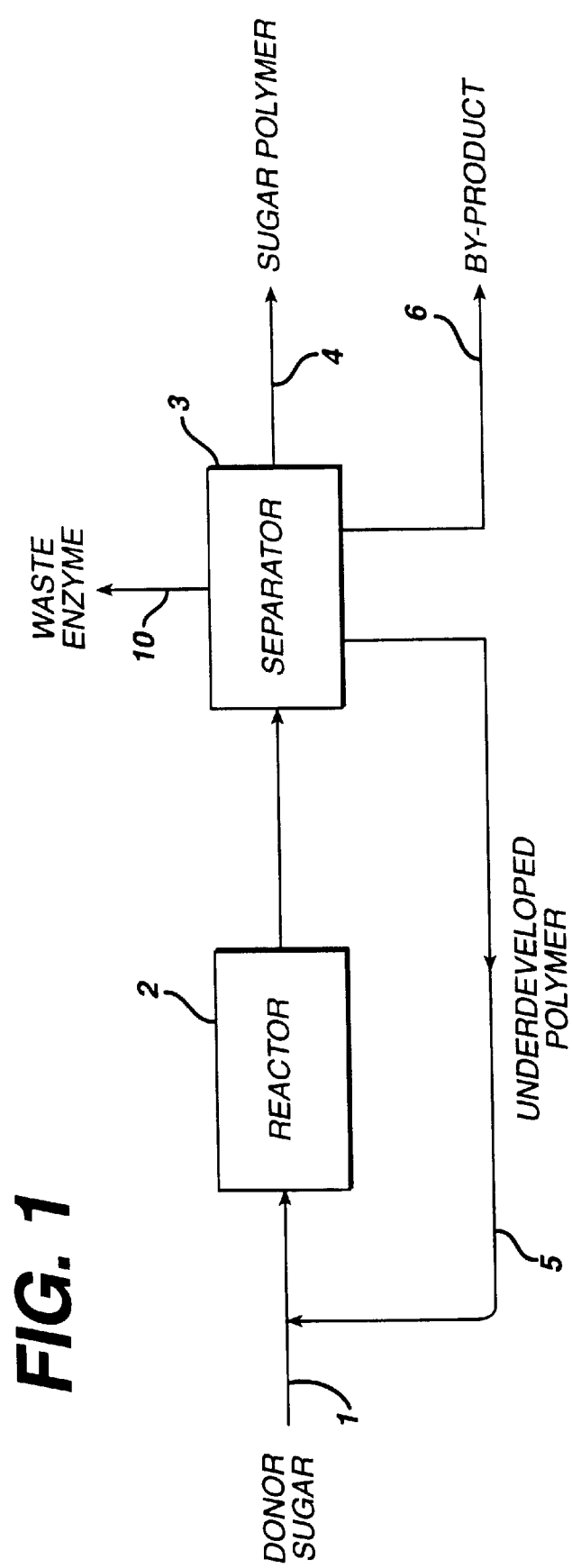
FIG. 1 illustrates the general scheme of the invention.

As shown in FIG. 1, a Sugar (carbohydrate) Donor (1) is fed to the Reactor (2) where the sugar polymer is elaborated. The crude product mixture is conveyed to a Separator (3) where the crude product is separated into a sugar polymer product (4), the underdeveloped polymer (5), which is carried back to reactor (2), and a by-product (6) of the polymerization.

Figure 2:
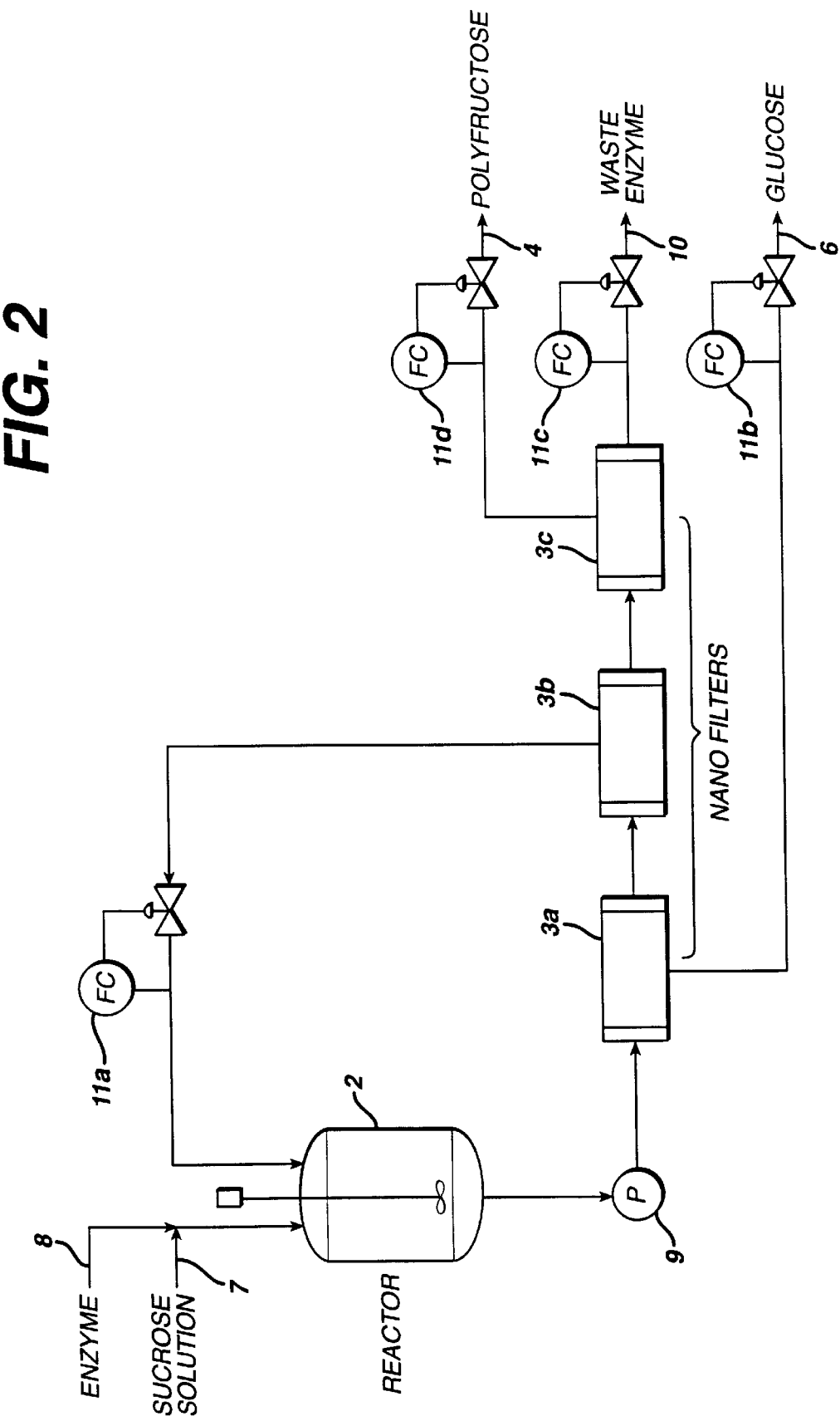
FIG. 2 illustrates one configuration of a combination membrane/enzyme system. Other possible configurations using batch, semi-batch, and continuous systems will be apparent to those skilled in the art.

FIG. 2 illustrates one example of how the general arrangement described in FIG. 1 can be employed to produce a fructose polymer from sucrose. A sucrose solution (7) and enzyme (8) are fed in a controlled manner into reactor (2) where sucrose is converted to the fructose polymer and glucose (by-product). Pump (9) meters out the crude mixture to the separator membranes (3a, 3b, and 3c). Membrane (3a) permeates mainly the glucose by-product (6). The concentrate is carried to membrane (3b) where sucrose and underdeveloped polymer chains, that is polymer chains which are not the desired length, (underdeveloped fructose polymer, 5a) is returned to the reactor. The concentrate containing product and enzyme is carried directly to a third membrane 3(c) which permeates the product (polyfructose (4)) away from the enzyme (10) in the concentrate stream. Flow control valves (11a–d) are positioned to enable control of the flow rates of effluents from the separator membranes (3a, 3b, 3c).

The following key advantages can be achieved with this invention:

1. The system allows the use of a cheap, readily available, and non-captive raw material.
2. Essentially 100% yield of any polymer length distribution can be achieved.
3. Additional reaction steps to avoid inhibition can be eliminated.
4. The system can use a series of inexpensive, available membranes or a continuous chromatographic system.
5. The membranes or chromatographic conditions can be quickly and inexpensively modified or reconfigured to produce any desired product distribution.
6. The system can be operated in a continuous mode allowing easy, consistent, operation.

Other benefits will be clear to those familiar with sugar processing.

The system is also very flexible in how enzyme can be utilized. In one form, fresh enzyme is added as an ingredient and deactivated enzyme periodically removed using a membrane to recover any sugars carried with the purge. In other cases the organism which produces the enzyme can be grown in the reactor. This is the case when the organism can grow at the reaction conditions and when it naturally over-expresses and excretes the required enzyme. In the case of inulin, yeasts that produce the fructose polymerization enzyme, e.g.; Aspergillus niger, A. japonicus Pullularia or Aureobasidium pullulans, Saccharomyces cerevisiae, etc., behave as just described. Further, they grow on the by-product of the reaction path, glucose. Processes which use fructosyl-transferases derived from Pullularia or Aureobasidium pullulans, and certain Aspergillus strains, useful in the preparation of fructans, are disclosed in the following: U.S. Pat. No. 4,309,505; U.S. Pat, No. 4,317,880; U.S. Pat, No. 4,335,207; U.S. Pat. Nos. 4,356,262; 4,423,150; U.S. Pat. No. 4,849,356.

We have also discovered that process chromatography can be used as an alternative to membranes to effect the separation. This would allow tighter fractionation at the expense of., slightly higher capital costs. Other systems that would provide classification of polymers by chain lengths, such as selective precipitation could also be used.

While we have described this new system in terms of inulin, it can readily be seen that it is applicable to the production of other linear and branched sugar polymers. Further, the system is useful in controlling the degree in which other functional sugars are added to a polymer chain.

It is interesting that this overall system mimics operations that normally occur in a plant. For example, in the chicory plant, a series of enzymatic reactions convert $CO_2$ and water to simple sugars which in turn, through another series of enzymatic reactions, get converted to the sugar polymers. These polymers are stored in the tuber of the chicory plant for use in the next growing season as an energy source to start the next growing cycle. In our system, other plants, such as sugar cane, provide the simple sugar and we provide the enzymes and reaction hardware to do the polymerization. For the case of sugar polymers, this combination draws the best part of the natural system and improves upon the plant's "production logistics". Consider a group of products based on polymers of fructose. It is conceivable to "design" a plant to produce each of these polymer products. Unlike inulin, which the plant produces for it own need, yields for our novel polymers would be based on how well we manipulate the plant's biochemical system to produce the desired material. A method to control chain length would also have to be built into the plant's natural "regulatory" system. We would then harvest the plant and extract the polymer. Each of these products would be subject to all of the overheads associated with its production and the risks associated with growing agricultural products. If the use of any of these products was large enough, these overheads and risk can be effectively absorbed, but for small volume products the cost could impose significant limitations. The advantage of separating the "mass produced" sucrose, from the "custom" produced polymers is clear. The economies of scale and agricultural risk abatement is captured in the common intermediate, sucrose, to all the low volume polymers while custom manufacturing is limited to only one part of the scheme, limiting overhead, capital, and eliminating all agricultural risk.

The following examples are intended to illustrate the invention but not to limit it:

EXAMPLE 1

Enzymatic Synthesis of Inulin as a Batch Process

Figure 3:
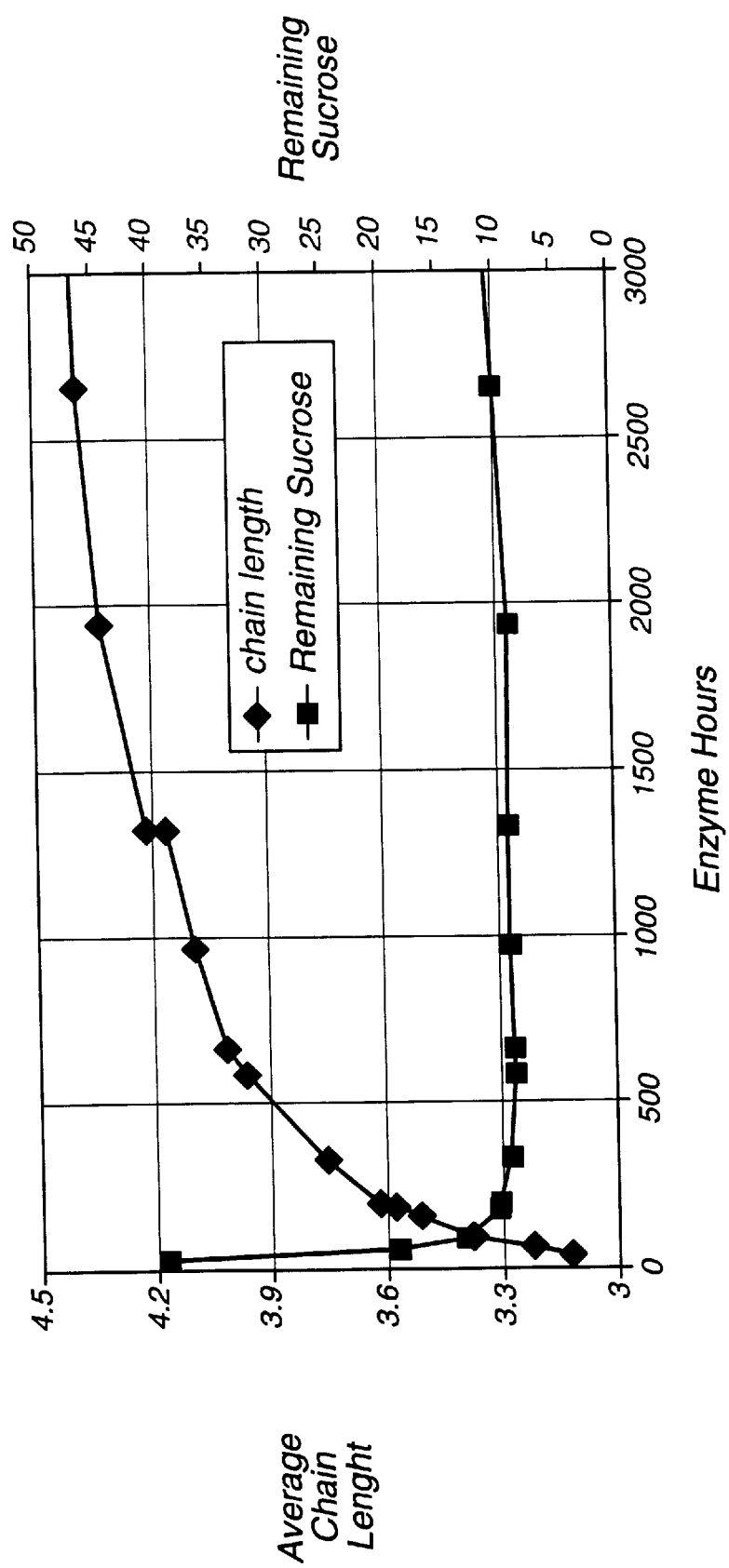
FIG. 3 is a graph illustrating the average chain length and remaining sucrose over enzyme-hours.

Fructosyl transferase (1000 Units/L) was added to 70-wt % sucrose solution. The mixtures were further diluted with water as needed to maintain 47-wt % sucrose and incubated at 50° C. for 3.33, 6.67 or 18 hours. Boiling for 10 minutes stopped the reactions. The carbohydrate composition was analyzed by HPLC. The carbohydrate compositions were determined to include unreacted sucrose, glucose, fructose, difructose and inulin of chain length DP3-DP7 (DP refers to degree of polymerization). FIG. 3 shows the effect of enzyme hours on chain length (♦) and remaining sucrose (■). Enzyme hours is defined as enzyme concentration (Units/kg sucrose) times residence time (hours).

EXAMPLE 2

Enzymatic Synthesis of Inulin as a Continuous Process

Figure 4:
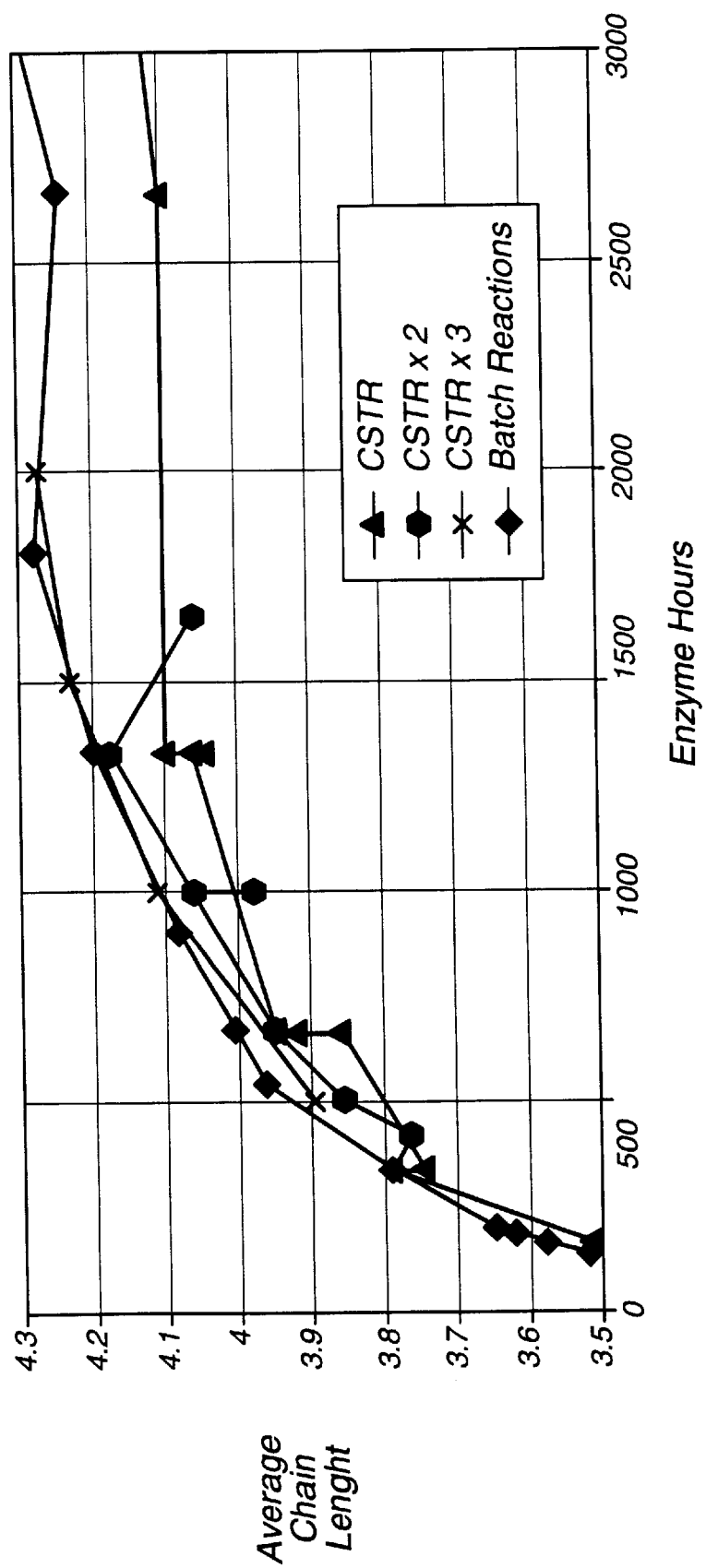
FIG. 4 is a graph illustrating the average chain length over enzyme-hours.

An aqueous sucrose solution (50-wt %) was pumped into a jacketed flask containing fructosyl transferase and sucrose solution. The contents of the jacketed flask were recirculated through a 30K MWCO hollow fiber membrane chosen to allow for permeation of all carbohydrates and retention of the fructosyl transferase. Permeate flow from the hollow fiber membrane was regulated to equal the flow of sugar solution into the jacketed flask. Permeate flow was directed to either a fraction collector, as in the case of a single ("CSTR"), or another jacketed flask containing fructosyl transferase, as in the case of a multiple CSTR. The contents of the jacketed flask were maintained at 50±2° C. A series of single and multiple CSTR's was performed varying enzyme concentration and residence time. The carbohydrate composition was analyzed by HPLC at each full residence. The carbohydrate compositions were determined to include unreacted sucrose, glucose, fructose, difructose and inulin of chain length DP3-DP7. FIG. 4 shows the effect of enzyme-hours (product of enzyme concentration in Units/L times the reaction time or residence time in hours) on chain length for single CSTR (▲), double CSTR (●), triple CSTR (✘) and batch reactions (♦).

EXAMPLE 3

Enzymatic Synthesis of Inulin During Byproduct Removal

Figure 5:
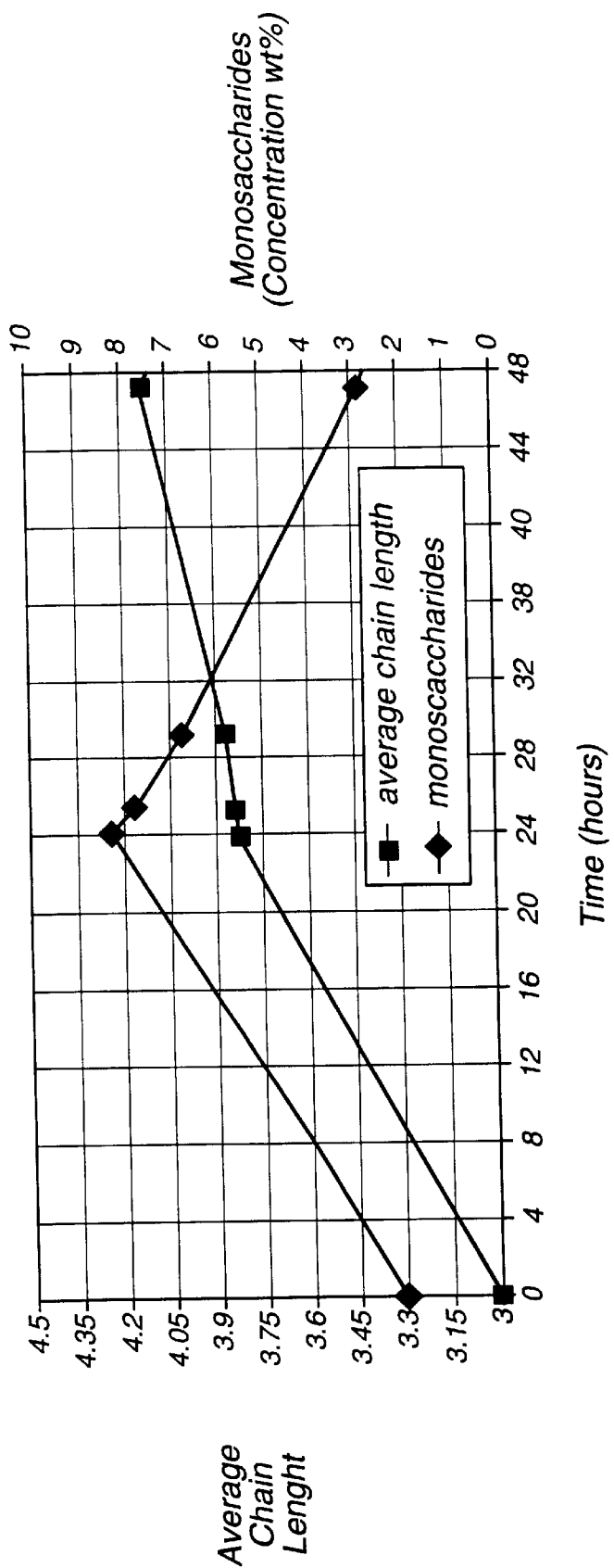
FIG. 5 is a graph illustrating the average chain length and monosaccharides over time.

Fructosyl transferase (40 Units/L) was added to a jacketed flask containing sucrose solution (50-wt %). The reaction was diluted with 1M citrate pH 5.5 and distilled water to obtain a solution of 20-wt % sucrose, 20 mM citrate pH 5.5 with an enzyme concentration of 15 Units/kg sucrose. The final solution was maintained at 50° C. for 24 hours with constant stirring. At the end of 24-hour reaction, the contents of the jacketed flask were recirculated through a membrane chosen to remove glucose selectively from the mixture of glucose, fructose, sucrose, difructose and inulin of chain length DP3–8. The permeate stream (glucose) was directed out of the jacketed flask and the volume lost to glucose removal was replaced by 20 mM citrate pH 5.5. Under this configuration, the enzymatic reaction was allowed to continue during glucose removal. FIG. 5 shows average chain length (■) increasing during glucose (♦) removal.

EXAMPLE 4

Recycled Sugars by Continuous Separation Using Membrane Separator

The crude reaction mixture as described in examples 1 or 2 was permeated through a 5000 NMWCO (Nominal Molecular Weight Cut-Off) membrane to retain the Fructosyltransferase and permeate all the carbohydrate. The carbohydrate stream was diluted with an equal volume of water then concentrated on a spiral wound membrane chosen such that molecules-with DP 3 or larger were mostly retained and DP 2 or smaller were mostly permeated. OSMONICS/ DESAL G10 was used in this case. The extents of partition between permeate and concentrate was calculated for each oligomer in the mixture. Calculated and observed values agreed within the error of the system. Three cycles of dilution and concentration were completed on the retained material. The final concentrate contained approximately 9–10% mono and disaccharides. The concentrate was diluted and reconcentrated three more times using a slightly tighter membrane (OSMONICS/DESAL G5) until the mono and disaccharide content was reduced to less than 5% of total sugars in solution. The combined permeates (about 80% mono and disaccharides based on dissolved sugars) were concentrated using a membrane chosen such that only the monosaccharides are permeated (OSMONICS/DESAL DL). The retained material contained disaccharides and lesser amounts of larger molecules that had been leaked through the previous membrane, and less than 60% monosaccharides. This was returned directly to the reactor, along with additional sucrose. The monosaccharide content can be reduced further by repeating cycles of dilution and reconcentration. Other membranes, such as OSMONICS/ DESAL G5 can be used instead of, or sequentially with, the DL to optimize removal of monosaccharides and recovery of desirable sugars in the recycle stream.

EXAMPLE 5

Recycled Sugars by Continuous Separation Using Chromatographic Separator

The crude reaction mixture as described in examples 1 or 2 was permeated through a 5000 NMWCO membrane to retain the Fructosyltransferase and permeate all the carbohydrate. The chromatographic separator employed was a Simulated Moving Bed (SMB) separator using ten columns (1"×19"). Feeds and take-offs started at the positions indicated by Table 1 below:

TABLE 1

| Column position | 1 | 2 | 4 | 5 | 10 |
|---|---|---|---|---|---|
| Crude feed |  |  |  | 2 mL/min |  |
| Eluant feed |  | 10 mL/min |  |  |  |
| Glucose take-off |  |  |  |  | 4.4 mL/min |
| Recycle take-off | 2.1 mL/min |  |  |  |  |
| Product takeoff |  |  | 5.5 mL/min |  |  |

The separator was operated in the typical manner for SMB such that the feed and take-off positions are advanced by one column with a fixed frequency (step time, 560 sec) while maintaining the same relative positions. A continuous recirculation of about 26 mL/min was maintained through the system. In the typical manner for SMB separations, the relative proportion of flows was periodically adjusted to maintain or change the desired separation. The composition of the exit streams is shown in Table 2 below:

TABLE 2

| Composition (%) | Glucose take-off | Recycle-take-off | Product take-off |
|---|---|---|---|
| Monosacharide | 85.9 | 60 | 2.2 |
| Disaccharide | 6.3 | 22.7 | 1.2 |
| Trisaccharide | 3.0 | 11.9 | 19.6 |
| Tetrasaccharide & larger | 4.8 | 5.4 | 77.0 |

EXAMPLE 6

Enzymatic Synthesis of Inulin With Recycle of Underdeveloped Polymers

Figure 6:
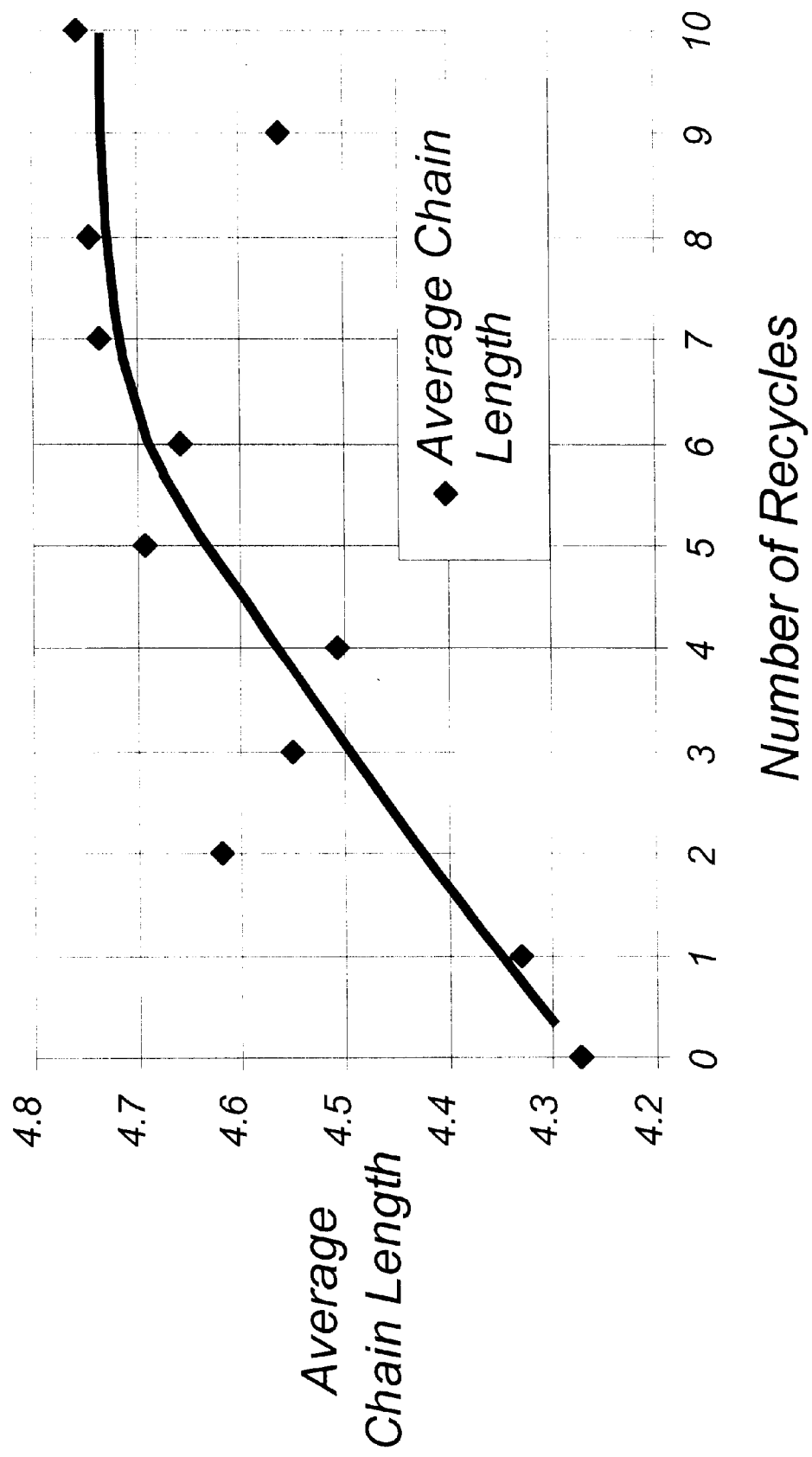
FIG. 6 is a graph illustrating the average DP length for chains of DP3+ over the number of recycles.

A series of inulin synthesis reactions were run at 50 wt % and 28 units of fructosyltransferase/g carbohydrate with an 18 hour incubation at 50° C. The carbohydrate composition of the starting material for the first reaction was 100% sucrose. The reaction was stopped by boiling and the final carbohydrate composition was analyzed by HPLC. The glucose byproduct was removed by chromatography. The remaining carbohydrates consisting of residual glucose, fructose, unreacted sucrose, and inulins of chain length DP3–7 were concentrated on a rotary evaporator and used as starting material in a subsequent inulin synthesis reaction. The carbohydrate compositions of subsequent reactions were about 20% recycled carbohydrates and 80% sucrose. Eleven reactions total were run. Ten reactions contained recycled carbohydrates. The FIG. 6 shows the rise in polymer chain length with each reaction containing recycled carbohydrates.

What is claimed is:

1. A process to produce straight or branched carbohydrate polymers comprising:
   a) transferring a monosaccharide or oligosaccharide residue from a carbohydrate donor to an acceptor by using an enzyme, thereby forming a reaction mixture containing by-products which inhibit the activity or selectivity of the enzyme and carbohydrate polymers;
   b) removing any by-products from the reaction mixture formed in step a) which may inhibit yield or selectivity of the enzyme;
   c) separating carbohydrate polymers which have not achieved the desired chain length from carbohydrate polymers which have achieved the desired chain length; and d) recycling the carbohydrate polymers which have not achieved the desired chain length to said transferring step.

2. The process of claim 1 where enzyme is a fructosyl transferase enzyme.

3. The process of claim 2 in which the enzyme used is produced in-situ by an appropriate organism.

4. The process of claim 1 wherein the carbohydrate donor is selected from the group consisting of a sugar nucleotide, a glycosyl phosphate, a disaccharide and an oligosaccharide.

5. The process of claim 4 wherein the monosaccharide or oligosaccharide is selected from the group consisting of glucose, galactose, fructose, fucose, sialic acid, N-acetyl glucosamine, N-acetyl galactosamine, glucuronic acid, iduronic acid xylose, and mannose.

6. The process of claim 1 wherein the carbohydrate polymer is a fructan.

7. The purpose in claim 1 where the process is continuous, batch, or semi-batch.

8. The process of claim 1, wherein the polymers are separated by using a method selected from the group consisting of chromatography and membrane separation.

9. The process of claim 1, wherein the desired chain length is from 3 to 10.

10. The process of claim 1, wherein the desired chain length is from 3 to 7.

11. A process for producing fructooligosaccharides which are linked via their reducing ends to an alpha-D-glucopyranosyl moiety comprising:

a) transferring fructose residues from sucrose to a fructooligosaccharide of the formula $GF_n$ where G is glucose, F is fructose and n is an integer between 1 and 60 by using a fructosyl-transferase, thereby forming a reaction mixture containing sucrose, glucose and fructooligosaccharides;

b) removing glucose and fructooligosaccharides having at least the desired value of n from the reaction mixture formed in step a) from fructooligosaccharides which have less than the desired value of n; and c) recycling the fructooligosaccharides which have less than the desired value of n to said transferring step.

12. The process of claim 11, wherein the desired value of n is between 3–10.

13. The process of claim 11, wherein the desired value of n is four or more.

14. The process of claim 11, wherein the glucose is mainly removed from the reaction mixture by membrane separation.

15. The process of claim 14, wherein after the reaction mixture has had mainly the glucose removed a concentrate mixture of mainly sucrose and fructooligosaccharides is formed, then the sucrose and the fructooligosaccharides with less than the desired value of n are separated from the fructooligosaccharides have at least the desired value of n.

16. The process of claim 11, wherein the transfer of glucose from sucrose to fructooligosaccharides occurs in a reaction vessel, a portion of the reaction mixture is removed from the reaction vessel and passed through a first membrane separation to remove mainly glucose from the reaction mixture thereby forming a concentrate mixture of mainly sucrose and fructooligosaccharides, passing the concentrate mixture through a second membrane separator to form a recycle stream containing mainly sucrose and fructooligosaccharides with less than the desired value of n, and a second stream containing fructooligosaccharides with at least the desired value of n.

17. The process of claim 16, wherein the recycle stream is returned to the reaction vessel.

* * * * *